(12) United States Patent
Carley et al.

(10) Patent No.: US 7,806,904 B2
(45) Date of Patent: **\*Oct. 5, 2010**

(54) CLOSURE DEVICE

(75) Inventors: Michael T. Carley, San Jose, CA (US); Richard S. Ginn, San Jose, CA (US); Javier Sagastegui, Castro Valley, CA (US); Janina Sagastegui, legal representative, Castro Valley, CA (US); Ronald J. Jabba, Redwood City, CA (US); William N. Aldrich, Napa, CA (US); W. Martin Belef, San Jose, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 529 days.

This patent is subject to a terminal disclaimer.

(21) Appl. No.: 10/787,073

(22) Filed: Feb. 24, 2004

(65) Prior Publication Data

US 2006/0135989 A1 Jun. 22, 2006

Related U.S. Application Data

(63) Continuation-in-part of application No. 10/335,075, filed on Dec. 31, 2002, now Pat. No. 7,211,101, which is a continuation-in-part of application No. 10/081,726, filed on Feb. 21, 2002, now Pat. No. 6,623,510, and a continuation-in-part of application No. 10/435,104, filed on May 9, 2003, and a continuation-in-part of application No. 09/732,178, filed on Dec. 7, 2000, now Pat. No. 6,719,777.

(51) Int. Cl.
*A61B 17/08* (2006.01)

(52) U.S. Cl. .................................................. 606/151

(58) Field of Classification Search .......... 606/219–221, 606/151–158, 213; 132/273–284
See application file for complete search history.

(56) References Cited

U.S. PATENT DOCUMENTS 287,046 A 10/1883 Norton
(Continued)

FOREIGN PATENT DOCUMENTS

CA 2 339 060 2/2000
(Continued)

OTHER PUBLICATIONS

Database WPI; Section PQ, Week 200120; Derwent Publications Ltd., London GB; AN 2001-203165; XP002199926 & ZA 200 100 528 A (Anthony T), Feb. 28, 2001 abstract.
(Continued)

*Primary Examiner*—Melanie Tyson
(74) *Attorney, Agent, or Firm*—Workman Nydegger

(57) ABSTRACT

A clip for engaging tissue includes a generally annular-shaped body defining a plane and disposed about a central axis extending normal to the plane. The body includes alternating inner and outer curved regions, defining a zigzag pattern about a periphery of the clip. The body is biased towards a planar configuration lying in the plane and deflectable towards a transverse configuration extending out of the plane. Tines extend from the inner curved regions, the tines being oriented towards the central axis in the planar configuration, and parallel to the central axis in the transverse configuration. The tines include primary tines and secondary tines that are shorter than the primary tines. The primary tines may be disposed on opposing inner curved regions and oriented towards one another. The primary tines are configured such that they are offset from the axes of symmetry of the curved regions from which they extend and are connected to the curved regions by curved or linear regions or are connected directly to the curved regions. The primary tines may overlap the body and may be of different lengths.

23 Claims, 3 Drawing Sheets

U.S. PATENT DOCUMENTS

| | | |
|---|---|---|
| 438,400 A | 10/1890 | Brennen |
| 1,088,393 A | 2/1914 | Backus |
| 1,331,401 A | 2/1920 | Summers |
| 1,426,111 A | 8/1922 | Sacker |
| 1,516,990 A | 11/1924 | Silverman |
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,951,482 A | 6/1960 | Sullivan |
| 2,944,311 A | 7/1960 | Schneckenberger |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |

| | | | | | |
|---|---|---|---|---|---|
| 5,061,274 A | 10/1991 | Kensey | 5,366,479 A | 11/1994 | McGarry et al. |
| 5,071,430 A | 12/1991 | de Salis et al. | 5,376,101 A | 12/1994 | Green et al. |
| 5,078,731 A | 1/1992 | Hayhurst | 5,383,896 A | 1/1995 | Gershony et al. |
| 5,092,941 A | 3/1992 | Miura | 5,383,905 A | 1/1995 | Golds et al. |
| 5,100,418 A | 3/1992 | Yoon et al. | RE34,866 E | 2/1995 | Kensey et al. |
| 5,100,422 A | 3/1992 | Berguer et al. | 5,391,173 A | 2/1995 | Wilk |
| 5,108,420 A | 4/1992 | Marks | 5,392,978 A | 2/1995 | Velez et al. |
| 5,108,421 A | 4/1992 | Fowler | 5,395,030 A | 3/1995 | Kuramoto et al. |
| 5,114,032 A | 5/1992 | Laidlaw | 5,409,499 A | 4/1995 | Yi |
| 5,114,065 A | 5/1992 | Storace | 5,411,520 A | 5/1995 | Nash et al. |
| 5,116,349 A | 5/1992 | Aranyi | 5,413,571 A | 5/1995 | Katsaros et al. |
| 5,122,122 A | 6/1992 | Allgood | 5,413,584 A | 5/1995 | Schulze |
| 5,122,156 A | 6/1992 | Granger et al. | 5,416,584 A | 5/1995 | Kay |
| 5,131,379 A | 7/1992 | Sewell, Jr. | 5,417,699 A | 5/1995 | Klein et al. |
| 5,147,381 A | 9/1992 | Heimerl et al. | 5,419,777 A | 5/1995 | Hofling |
| 5,156,609 A | 10/1992 | Nakao et al. | 5,423,857 A | 6/1995 | Rosenman et al. |
| 5,158,566 A | 10/1992 | Pianetti | 5,425,489 A | 6/1995 | Shichman et al. |
| 5,160,339 A | 11/1992 | Chen et al. | 5,425,740 A | 6/1995 | Hutchinson, Jr. |
| 5,167,634 A | 12/1992 | Corrigan, Jr. et al. | 5,431,639 A | 7/1995 | Shaw |
| 5,167,643 A | 12/1992 | Lynn | 5,431,667 A | 7/1995 | Thompson et al. |
| 5,171,249 A | 12/1992 | Stefanchik et al. | 5,433,721 A | 7/1995 | Hooven et al. |
| 5,171,250 A | 12/1992 | Yoon | 5,437,631 A | 8/1995 | Janzen |
| 5,171,251 A | 12/1992 | Bregen et al. | 5,439,479 A | 8/1995 | Shichman et al. |
| 5,176,648 A | 1/1993 | Holmes et al. | 5,443,477 A | 8/1995 | Marin et al. |
| 5,176,682 A | 1/1993 | Chow | 5,443,481 A | 8/1995 | Lee |
| 5,192,288 A | 3/1993 | Thompson et al. | 5,449,359 A | 9/1995 | Groiso |
| 5,192,300 A | 3/1993 | Fowler | 5,456,400 A | 10/1995 | Shichman et al. |
| 5,192,301 A | 3/1993 | Kamiya et al. | 5,462,558 A | 10/1995 | Kolesa et al. |
| 5,192,302 A | 3/1993 | Kensey et al. | 5,462,561 A | 10/1995 | Voda |
| 5,192,602 A | 3/1993 | Spencer et al. | 5,466,241 A | 11/1995 | Leroy et al. |
| 5,203,787 A | 4/1993 | Noblitt et al. | 5,470,010 A | 11/1995 | Rothfuss et al. |
| 5,209,756 A | 5/1993 | Seedhorn et al. | 5,474,557 A | 12/1995 | Mai |
| 5,217,024 A | 6/1993 | Dorsey et al. | 5,474,572 A | 12/1995 | Hayhurst |
| 5,219,359 A | 6/1993 | McQuilkin et al. | 5,478,352 A | 12/1995 | Fowler |
| 5,222,974 A | 6/1993 | Kensey et al. | 5,478,353 A | 12/1995 | Yoon et al. |
| 5,226,908 A | 7/1993 | Yoon | 5,478,354 A | 12/1995 | Tovey et al. |
| 5,234,449 A | 8/1993 | Bruker et al. | 5,486,195 A | 1/1996 | Myers et al. |
| 5,236,435 A | 8/1993 | Sewell, Jr. | 5,497,933 A | 3/1996 | DeFonzo et al. |
| 5,236,445 A | 8/1993 | Hayhurst et al. | 5,501,698 A | 3/1996 | Roth et al. |
| 5,242,457 A | 9/1993 | Akopov et al. | 5,507,744 A | 4/1996 | Tay et al. |
| 5,242,459 A | 9/1993 | Buelna | 5,507,755 A | 4/1996 | Gresl et al. |
| 5,246,156 A | 9/1993 | Rothfuss et al. | 5,514,159 A | 5/1996 | Matula et al. |
| 5,246,443 A | 9/1993 | Mai | 5,521,184 A | 5/1996 | Zimmermann |
| 5,250,058 A | 10/1993 | Miller et al. | 5,522,840 A | 6/1996 | Krajicek |
| 5,254,105 A | 10/1993 | Haaga | 5,527,322 A | 6/1996 | Klein et al. |
| 5,258,015 A | 11/1993 | Li et al. | 5,536,251 A | 7/1996 | Evard et al. |
| 5,269,792 A | 12/1993 | Kovac et al. | 5,540,712 A | 7/1996 | Kleshinski et al. |
| 5,275,616 A | 1/1994 | Fowler | 5,540,716 A | 7/1996 | Hlavacek |
| 5,282,808 A | 2/1994 | Kovac et al. | 5,543,520 A | 8/1996 | Zimmermann |
| 5,282,827 A | 2/1994 | Kensey et al. | 5,544,802 A | 8/1996 | Crainich |
| 5,282,832 A | 2/1994 | Toso et al. | 5,547,474 A | 8/1996 | Kloeckl et al. |
| 5,289,963 A | 3/1994 | McGarry et al. | 5,560,532 A | 10/1996 | DeFonzo et al. |
| 5,290,243 A | 3/1994 | Chodorow et al. | 5,571,120 A | 11/1996 | Yoon |
| 5,290,310 A | 3/1994 | Makower et al. | 5,575,771 A | 11/1996 | Walinsky |
| 5,292,309 A | 3/1994 | Van Tassel et al. | 5,584,879 A | 12/1996 | Reimold et al. |
| 5,292,332 A | 3/1994 | Lee | 5,591,205 A | 1/1997 | Fowler |
| 5,304,184 A | 4/1994 | Hathaway et al. | 5,593,412 A | 1/1997 | Martinez et al. |
| 5,304,204 A | 4/1994 | Bregen | 5,593,422 A | 1/1997 | Muijs Van de Moer et al. |
| 5,306,254 A | 4/1994 | Nash et al. | 5,593,425 A | 1/1997 | Bonutti et al. |
| 5,306,280 A | 4/1994 | Bregen et al. | 5,601,602 A | 2/1997 | Fowler |
| 5,318,542 A | 6/1994 | Hirsch et al. | 5,609,597 A | 3/1997 | Lehrer |
| 5,320,639 A | 6/1994 | Rudnick | 5,611,986 A | 3/1997 | Datta et al. |
| 5,330,442 A | 7/1994 | Green et al. | 5,613,974 A | 3/1997 | Andreas et al. |
| 5,330,445 A | 7/1994 | Haaga | 5,618,291 A | 4/1997 | Thompson et al. |
| 5,334,216 A | 8/1994 | Vidal et al. | 5,618,306 A | 4/1997 | Roth et al. |
| 5,334,217 A | 8/1994 | Das | 5,620,452 A | 4/1997 | Yoon |
| 5,335,680 A | 8/1994 | Moore | 5,620,461 A | 4/1997 | Muijs et al. |
| 5,340,360 A | 8/1994 | Stefanchik | 5,630,824 A | 5/1997 | Hart |
| 5,350,399 A | 9/1994 | Erlebacher et al. | 5,643,318 A | 7/1997 | Tsukernik et al. |
| 5,352,229 A | 10/1994 | Goble et al. | 5,645,553 A | 7/1997 | Kolesa et al. |
| 5,364,406 A | 11/1994 | Sewell, Jr. | 5,645,565 A | 7/1997 | Rudd et al. |
| 5,364,408 A | 11/1994 | Gordon | 5,645,566 A | 7/1997 | Brenneman et al. |
| 5,366,458 A | 11/1994 | Korthoff et al. | 5,645,567 A | 7/1997 | Crainich |

| | | | | | |
|---|---|---|---|---|---|
| 5,649,959 A | 7/1997 | Hannam et al. | 5,871,525 A | 2/1999 | Edwards et al. |
| D383,539 S | 9/1997 | Croley | 5,873,876 A | 2/1999 | Christy |
| 5,669,917 A | 9/1997 | Sauer et al. | 5,879,366 A | 3/1999 | Shaw et al. |
| 5,674,231 A | 10/1997 | Green et al. | 5,893,592 A | 4/1999 | Schulze et al. |
| 5,676,689 A | 10/1997 | Kensey et al. | 5,897,487 A | 4/1999 | Ouchi |
| 5,676,974 A | 10/1997 | Valdes et al. | 5,902,310 A | 5/1999 | Foerster et al. |
| 5,681,334 A | 10/1997 | Evans et al. | 5,904,697 A * | 5/1999 | Gifford et al. ............... 606/155 |
| 5,681,351 A | 10/1997 | Jamiolkowski et al. | 5,906,631 A | 5/1999 | Imran |
| 5,683,405 A | 11/1997 | Yacoubian et al. | 5,907,893 A | 6/1999 | Zadno-Azizi et al. |
| 5,690,674 A | 11/1997 | Diaz | 5,910,155 A | 6/1999 | Ratcliff et al. |
| 5,695,504 A | 12/1997 | Gifford, III et al. | 5,919,207 A | 7/1999 | Taheri |
| 5,695,505 A | 12/1997 | Yoon | 5,919,208 A | 7/1999 | Valenti |
| 5,695,524 A | 12/1997 | Kelley et al. | 5,922,009 A | 7/1999 | Epstein et al. |
| 5,700,273 A | 12/1997 | Buelna et al. | 5,935,147 A | 8/1999 | Kensey et al. |
| 5,709,708 A | 1/1998 | Thal | 5,938,667 A | 8/1999 | Peyser et al. |
| 5,716,375 A | 2/1998 | Fowler | 5,941,890 A | 8/1999 | Voegele et al. |
| 5,720,755 A | 2/1998 | Dakov | 5,947,999 A | 9/1999 | Groiso |
| 5,720,765 A | 2/1998 | Thal | 5,951,518 A | 9/1999 | Licata et al. |
| 5,725,498 A | 3/1998 | Janzen et al. | 5,951,576 A | 9/1999 | Wakabayashi |
| 5,725,552 A | 3/1998 | Kotula et al. | 5,951,589 A | 9/1999 | Epstein et al. |
| 5,725,554 A | 3/1998 | Simon et al. | 5,957,936 A | 9/1999 | Yoon et al. |
| 5,725,556 A | 3/1998 | Moser et al. | 5,957,938 A | 9/1999 | Zhu et al. |
| 5,728,109 A | 3/1998 | Schulze et al. | 5,964,782 A | 10/1999 | Lafontaine et al. |
| 5,728,110 A | 3/1998 | Vidal et al. | 5,976,159 A | 11/1999 | Bolduc et al. |
| 5,728,114 A | 3/1998 | Evans et al. | 5,976,161 A | 11/1999 | Kirsch et al. |
| 5,728,122 A | 3/1998 | Leschinsky et al. | 5,984,934 A | 11/1999 | Ashby et al. |
| 5,728,132 A | 3/1998 | Van Tassel et al. | 5,984,949 A | 11/1999 | Levin |
| 5,732,872 A | 3/1998 | Bolduc et al. | 5,993,468 A | 11/1999 | Rygaard |
| 5,735,873 A | 4/1998 | MacLean | 5,993,476 A | 11/1999 | Groiso |
| 5,735,875 A | 4/1998 | Bonutti et al. | 6,001,110 A | 12/1999 | Adams |
| 5,735,877 A | 4/1998 | Pagedas | 6,004,341 A | 12/1999 | Zhu et al. |
| 5,749,898 A | 5/1998 | Schulze et al. | 6,007,563 A | 12/1999 | Nash et al. |
| 5,752,966 A | 5/1998 | Chang | 6,013,084 A | 1/2000 | Ken et al. |
| 5,755,726 A | 5/1998 | Pratt et al. | 6,022,372 A | 2/2000 | Kontos |
| 5,755,778 A | 5/1998 | Kleshinski | 6,024,750 A | 2/2000 | Mastri |
| 5,766,217 A | 6/1998 | Christy | 6,024,758 A | 2/2000 | Thal |
| 5,766,246 A | 6/1998 | Mulhauser et al. | 6,030,364 A | 2/2000 | Durgin et al. |
| 5,769,862 A | 6/1998 | Kammerer et al. | 6,030,413 A | 2/2000 | Lazarus |
| 5,769,870 A | 6/1998 | Salahieh et al. | 6,033,427 A | 3/2000 | Lee |
| 5,776,150 A | 7/1998 | Nolan et al. | 6,036,703 A | 3/2000 | Evans et al. |
| 5,779,707 A | 7/1998 | Bertholet et al. | 6,036,720 A | 3/2000 | Abrams et al. |
| 5,782,844 A | 7/1998 | Yoon et al. | 6,045,570 A | 4/2000 | Epstein et al. |
| 5,782,860 A | 7/1998 | Epstein et al. | 6,048,358 A | 4/2000 | Barak |
| 5,782,861 A | 7/1998 | Cragg et al. | 6,056,768 A | 5/2000 | Cates et al. |
| 5,782,864 A | 7/1998 | Lizardi | 6,056,769 A | 5/2000 | Epstein et al. |
| 5,795,958 A | 8/1998 | Rao et al. | 6,056,770 A | 5/2000 | Epstein et al. |
| 5,797,928 A | 8/1998 | Kogasaka | 6,059,800 A | 5/2000 | Hart et al. |
| 5,797,931 A | 8/1998 | Bito et al. | 6,063,085 A | 5/2000 | Tay et al. |
| 5,797,933 A | 8/1998 | Snow et al. | 6,063,114 A | 5/2000 | Nash et al. |
| 5,797,958 A | 8/1998 | Yoon | 6,066,160 A | 5/2000 | Colvin et al. |
| 5,810,776 A | 9/1998 | Bacich et al. | 6,071,300 A | 6/2000 | Brenneman et al. |
| 5,810,846 A | 9/1998 | Virnich et al. | 6,074,409 A | 6/2000 | Goldfarb |
| 5,810,851 A | 9/1998 | Yoon | 6,077,281 A | 6/2000 | Das |
| 5,810,877 A | 9/1998 | Roth et al. | 6,077,291 A | 6/2000 | Das |
| 5,814,069 A | 9/1998 | Schulze et al. | 6,080,182 A | 6/2000 | Shaw et al. |
| 5,817,113 A | 10/1998 | Gifford, III et al. | 6,080,183 A | 6/2000 | Tsugita et al. |
| 5,820,631 A | 10/1998 | Nobles | 6,086,608 A | 7/2000 | Ek et al. |
| 5,827,298 A | 10/1998 | Hart et al. | 6,090,130 A | 7/2000 | Nash et al. |
| 5,830,125 A | 11/1998 | Scribner et al. | 6,092,561 A | 7/2000 | Schmid |
| 5,833,698 A | 11/1998 | Hinchliffe et al. | 6,099,553 A | 8/2000 | Hart et al. |
| 5,843,167 A | 12/1998 | Dwyer et al. | 6,102,271 A | 8/2000 | Longo et al. |
| 5,846,254 A | 12/1998 | Schulze et al. | 6,106,545 A | 8/2000 | Egan |
| 5,853,421 A | 12/1998 | Leschinsky et al. | 6,110,184 A | 8/2000 | Weadock |
| 5,853,422 A | 12/1998 | Huebsch et al. | 6,113,612 A | 9/2000 | Swanson et al. |
| 5,855,312 A | 1/1999 | Toledano | 6,117,125 A | 9/2000 | Rothbarth et al. |
| 5,858,082 A | 1/1999 | Cruz et al. | 6,117,148 A | 9/2000 | Ravo |
| 5,860,991 A | 1/1999 | Klein et al. | 6,120,524 A | 9/2000 | Taheri |
| 5,861,005 A | 1/1999 | Kontos | 6,126,675 A | 10/2000 | Schervinsky et al. |
| 5,868,755 A | 2/1999 | Kanner et al. | 6,126,677 A | 10/2000 | Ganaja et al. |
| 5,868,763 A | 2/1999 | Spence et al. | 6,136,010 A | 10/2000 | Modesitt et al. |
| 5,871,474 A | 2/1999 | Hermann et al. | 6,143,017 A | 11/2000 | Thal |
| 5,871,490 A | 2/1999 | Schulze et al. | 6,149,660 A | 11/2000 | Laufer et al. |
| 5,871,501 A | 2/1999 | Leschinsky et al. | 6,149,667 A | 11/2000 | Hovland et al. |

| | | |
|---|---|---|
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,165,204 A | 12/2000 | Levinson et al. |
| 6,174,324 B1 | 1/2001 | Egan et al. |
| 6,193,734 B1 | 2/2001 | Bolduc et al. |
| 6,197,042 B1 | 3/2001 | Ginn et al. |
| 6,200,329 B1 | 3/2001 | Fung et al. |
| 6,203,565 B1 | 3/2001 | Bonutti et al. |
| 6,206,913 B1 | 3/2001 | Yencho et al. |
| 6,220,248 B1 | 4/2001 | Voegele et al. |
| 6,221,102 B1 | 4/2001 | Baker et al. |
| 6,231,592 B1 | 5/2001 | Bonutti et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,305,891 B1 | 10/2001 | Burlingame |
| 6,319,258 B1 | 11/2001 | McAllen, III et al. |
| 6,322,580 B1 | 11/2001 | Kanner |
| 6,334,865 B1 | 1/2002 | Redmond et al. |
| 6,348,064 B1 | 2/2002 | Kanner |
| 6,358,258 B1 | 3/2002 | Arcia et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 * | 12/2002 | Spence et al. ............... 606/153 |
| 6,500,115 B2 | 12/2002 | Krattiger et al. |
| 6,506,210 B1 | 1/2003 | Kanner |
| 6,517,569 B2 | 2/2003 | Mikus et al. |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,623,509 B2 | 9/2003 | Ginn |
| 6,623,510 B2 | 9/2003 | Carley et al. |
| 6,626,918 B1 | 9/2003 | Ginn et al. |
| 6,632,238 B2 | 10/2003 | Ginn et al. |
| 6,634,537 B2 | 10/2003 | Chen |
| 6,645,205 B2 | 11/2003 | Ginn |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,926,723 B1 | 8/2005 | Mulhauser et al. |
| 6,926,731 B2 | 8/2005 | Coleman et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,083,635 B2 | 8/2006 | Ginn |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 * | 5/2007 | Carley et al. ............... 606/213 |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,533,790 B1 | 5/2009 | Knodel et al. |
| 7,597,706 B2 | 10/2009 | Kanner et al. |
| D611,144 S | 3/2010 | Reynolds |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026208 A1 | 2/2002 | Belef |
| 2002/0026215 A1 | 2/2002 | Redmond et al. |
| 2002/0038127 A1 | 3/2002 | Blatter et al. |
| 2002/0042622 A1 | 4/2002 | Vargas et al. |
| 2002/0049472 A1 | 4/2002 | Coleman et al. |
| 2002/0058960 A1 | 5/2002 | Hudson et al. |
| 2002/0072768 A1 | 6/2002 | Ginn |

| | | |
|---|---|---|
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0193808 A1 | 12/2002 | Belef et al. |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0032981 A1 | 2/2003 | Kanner et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0158577 A1 | 8/2003 | Ginn et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0165357 A1 | 7/2005 | McGuckin et al. |
| 2005/0177189 A1 | 8/2005 | Ginn et al. |
| 2005/0216057 A1 | 9/2005 | Coleman et al. |
| 2005/0222614 A1 | 10/2005 | Ginn et al. |
| 2005/0234508 A1 | 10/2005 | Cummins et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1* | 12/2005 | Loshakove et al. .......... 606/213 |
| 2006/0020270 A1 | 1/2006 | Jabba et al. |
| 2006/0034930 A1 | 2/2006 | Khosravi et al. |
| 2006/0047313 A1 | 3/2006 | Khanna et al. |
| 2006/0100664 A1 | 5/2006 | Pai et al. |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0253037 A1 | 11/2006 | Ginn et al. |
| 2006/0253072 A1 | 11/2006 | Pai et al. |
| 2006/0265012 A1 | 11/2006 | Anderson |
| 2006/0287674 A1 | 12/2006 | Ginn et al. |
| 2007/0010853 A1 | 1/2007 | Ginn et al. |
| 2007/0010854 A1 | 1/2007 | Cummins |
| 2007/0021778 A1 | 1/2007 | Carly |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0123817 A1 | 5/2007 | Khosravi et al. |
| 2007/0203506 A1 | 8/2007 | Sibbitt, Jr. et al. |
| 2007/0250080 A1 | 10/2007 | Jones et al. |
| 2007/0270904 A1 | 11/2007 | Ginn |
| 2007/0276416 A1 | 11/2007 | Ginn et al. |
| 2007/0282352 A1 | 12/2007 | Carley et al. |
| 2008/0004636 A1 | 1/2008 | Walberg |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0221616 A1 | 9/2008 | Ginn et al. |
| 2008/0312686 A1 | 12/2008 | Ellingwood |
| 2008/0319475 A1 | 12/2008 | Clark |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0254119 A1 | 10/2009 | Sibbitt, Jr. et al. |
| 2010/0130965 A1 | 5/2010 | Sibbitt, Jr. |

FOREIGN PATENT DOCUMENTS

| | | |
|---|---|---|
| DE | 197 11 288 | 1/1998 |
| DE | 297 23 736 U 1 | 4/1999 |
| DE | 19859952 | 2/2000 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0452 | 12/2002 |
| IE | S 2002/0664 | 2/2003 |
| IE | S 2002/0665 | 2/2003 |
| IE | S 2002/0451 | 7/2003 |
| IE | S 2002/0552 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| JP | 58-181006 | 12/1983 |
| JP | 12 74750 | 11/1989 |
| JP | 11500642 | 8/1997 |

| | | |
|---|---|---|
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/094748 | 11/2003 |
| WO | WO 03/101310 | 12/2003 |
| WO | WO 03/071957 | 1/2004 |
| WO | WO 2004/004578 | 1/2004 |
| WO | WO 2004/060169 | 7/2004 |
| WO | WO 2004/069054 | 8/2004 |
| WO | WO 2005/000126 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2008/031102 | 9/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/25014 | 3/2007 |
| WO | WO 2007/25017 | 3/2007 |
| WO | WO 2007/25018 | 3/2007 |
| WO | WO 2007/25019 | 3/2007 |
| WO | WO 2007/81836 | 7/2007 |
| WO | WO 2009/079091 | 6/2009 |
| WO | WO 2010/031050 | 3/2010 |
| ZA | 20010527 | 1/2001 |
| ZA | 200100528 | 1/2001 |

OTHER PUBLICATIONS

"Hand tool for forming telephone connections—comprises pliers with reciprocably driven ram crimping clip around conductors against anvil", Derwent-ACC-No. 1978-B8090A.
U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
2002/0072768, Office Action, Aug. 27, 2004.
2002/0072768, Office Action, Feb. 23, 2005.
2002/0072768, Office Action, Apr. 11, 2005.
2002/0072768, Office Action, Jul. 27, 2005.
2002/0072768, Office Action, Mar. 6, 2006.
2002/0072768, Office Action, May 24, 2006.
2002/0072768, Office Action, Oct. 26, 2006.
2002/0072768, Office Action, Apr. 19, 2007.
2002/0133193, Office Action, Nov. 4, 2004.
2002/0133193, Office Action, May 4, 2005.
2002/0133193, Office Action, Oct. 18, 2005.
2002/0133193, Notice of Allowance, Apr. 18, 2007.
2002/0133193, Notice of Allowance, Sep. 27, 2007.
2003/0078598, Office Action, Feb. 9, 2005.
2003/0078598, Office Action, May 26, 2005.
2003/0078598, Office Action, Oct. 4, 2005.
2003/0078598, Notice of Allowance, May 10, 2006.
2003/0078598, Notice of Allowance, Jul. 2, 2007.
2003/0195561, Office Action, Jun. 10, 2004.
2003/0195561, Notice of Allowance, Sep. 21, 2004.
2003/0195561, Office Action, Jan. 3, 2006.
2003/0195561, Issue Notification, Feb. 15, 2006.
2003/0195561, Office Action, May 16, 2006.
2003/0195561, Notice of Allowance, Dec. 28, 2006.
2003/0195561, Notice of Allowance, Jul. 10, 2007.
2003/0195561, Notice of Allowance, Aug. 2, 2007.
2004/0153123, Office Action, Sep. 22, 2006.
2004/0153123, Office Action, Jan. 31, 2007.
2004/0153123, Office Action, Sep. 18, 2007.
2004/0153122, Office Action, Nov. 30, 2005.
2004/0153122, Office Action, Aug. 23, 2006.
2004/0153122, Office Action, Feb. 13, 2007.
2004/0153122, Office Action, Sep. 12, 2007.
2004/0073255, Office Action, Sep. 15, 2006.
2004/0073255, Office Action, Apr. 18, 2007.
2004/0073236, Office Action, Sep. 19, 2006.
2004/0073236, Office Action, May 2, 2007.
2004/0009289, Office Action, Jun. 30, 2006.
2004/0009289, Office Action, Oct. 20, 2006.
2004/0009289, Office Action, May 29, 2007.
2005/0274768, Office Action, Oct. 19, 2006.
2005/0274768, Office Action, Aug. 10, 2007.
2005/0216057, Office Action, Feb. 6, 2007.

2005/0216057, Office Action, May 30, 2007.
2006/0195124, Office Action, Jun. 6, 2007.
2006/0195123, Office Action, May 14, 2007.
2005/0234508, Office Action, Aug. 13, 2007.
2004/0167570, Office Action, Oct. 30, 2006.
2004/0167570, Office Action, Apr. 17, 2007.
2004/0167570, Office Action, Aug. 31, 2007.
6,277,140, Office Action, Mar. 26, 2001.
6,277,140, Notice of Allowance, Jun. 4, 2001.
6,277,140, Issue Notification, Aug. 6, 2001.
6,197,042, Notice of Allowance, Nov. 6, 2000.
6,197,042, Issue Notification, Feb. 15, 2001.
6,391,048, Notice of Allowance, Mar. 26, 2001.
6,391,048, Office Action, Sep. 5, 2001.
6,391,048, Notice of Allowance, Feb. 11, 2002.
6,391,048, Issue Notification, May 3, 2002.
6,461,364, Notice of Allowance, May 6, 2002.
6,461,364, Issue Notification, Sep. 19, 2002.
6,582,452, Notice of Allowance, Jan. 31, 2003.
6,582,452, Issue Notification, Jun. 5, 2003.
6,616,686, Office Action, Dec. 17, 2002.
6,616,686, Notice of Allowance, Apr. 21, 2003.
6,616,686, Issue Notification, Aug. 21, 2003.
6,623,510, Notice of Allowance, Apr. 11, 2003.
6,623,510, Office Action, Jun. 9, 2003.
6,623,510, Issue Notification, Sep. 4, 2003.
6,632,238, Office Action, Feb. 26, 2003.
6,632,238, Notice of Allowance, Jun. 16, 2003.
6,632,238, Issue Notification, Sep. 25, 2003.
6,669,714, Office Action, Mar. 4, 2003.
6,669,714, Notice of Allowance, Jul. 28, 2003.
6,669,714, Issue Notification, Dec. 11, 2003.
6,695,867, Notice of Allowance, Sep. 29, 2003.
6,695,867, Issue Notification, Feb. 5, 2004.
6,719,777, Office Action, Feb. 20, 1987.
6,719,777, Notice of Allowance, Jul. 24, 1987.
6,719,777, Issue Notification, Mar. 25, 2004.
6,749,621, Notice of Allowance, Feb. 9, 2004.
6,749,621, Office Action, Apr. 13, 2004.
6,749,621, Issue Notification, May 27, 2004.
6,780,197, Office Action, Sep. 11, 2003.
6,780,197, Office Action, Feb. 9, 2004.
6,780,197, Notice of Allowance, Mar. 17, 2004.
6,780,197, Issue Notification, Aug. 5, 2004.
6,926,731, Office Action, Nov. 16, 2004.
6,926,731, Notice of Allowance, Apr. 6, 2005.
6,926,731, Issue Notification, Jul. 20, 2005.
6,942,674, Office Action, Sep. 29, 2004.
6,942,674, Notice of Allowance, May 13, 2005.
6,942,674, Issue Notification, Aug. 24, 2005.
7,001,398, Office Action, Mar. 22, 2005.
7,001,398, Notice of Allowance, Jul. 6, 2005.
7,001,398, Notice of Allowance, Oct. 5, 2005.
7,001,398, Issue Notification, Feb. 21, 2006.
7,008,435, Office Action, Apr. 20, 2005.
7,008,435, Office Action, Aug. 10, 2005.
7,008,435, Notice of Allowance, Oct. 18, 2005.
7,008,435, Issue Notification, Feb. 15, 2006.
7,108,709, Office Action, Jul. 27, 2004.
7,108,709, Office Action, Dec. 17, 2004.
7,108,709, Notice of Allowance, Mar. 9, 2005.
7,108,709, Office Action, Aug. 11, 2006.
7,108,709, Issue Notification, Aug. 30, 2006.
7,111,768, Office Action, Feb. 23, 2006.
7,111,768, Notice of Allowance, May 31, 2006.
7,111,768, Issue Notification, Sep. 6, 2006.
7,163,551, Office Action, Jan. 10, 2006.
7,163,551, Notice of Allowance, Sep. 20, 2006.
7,163,551, Issue Notification, Dec. 27, 2006.
7,211,101, Office Action, Aug. 10, 2005.
7,211,101, Office Action, Dec. 19, 2005.
7,211,101, Office Action, Apr. 21, 2006.
7,211,101, Notice of Allowance, Dec. 27, 2006.

7,211,101, Issue Notification, Apr. 11, 2007.
2006/0144479, Office Action, Oct. 16, 2007.
Stretch Comb by Scunci, retrieved via internet at www.scunci.com/productdetail by examiner on Oct. 9, 2007, publication date unavailable.
Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62-No. 8, Section of Transplantation Surgery Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77-No. 5, Department of Anesthesia, Children's Hospital, Boston, MA.
E Pikoulis et al, Arterial reconstruction with vascular clips is safe and quicker than sutured repair, Cardiovascular Surgery, Dec. 1988, pp. 573-578(6), vol. 6-No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of Cardiology, Aug. 1993, pp. 445-449, vol. 72-No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5-No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42-No. 3, Division of Neurosurgery, University of Alberta, Edmonton, Canada.
Jeremy L Gilbert PHD, Wound Closure Biomaterials And Devices, Shock., Mar. 1999, p. 226, vol. 11-No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School, Hannover, Germany.
K Narayanan et al, Simultaneous primary closure of four fasciotomy wounds in a single setting using the Sure-Closure device, Injury, Jul. 1996, pp. 449-451, vol. 27-No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6-No. 5, Orlando Regional Medical Center, FL.
Michael Gianturco, A Play on Catheterization, Forbes, Dec. 1996, p. 146, vol. 158-No. 15.
Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183-No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63-No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45-No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular And Interventional Radiology 1996, Nov.-Dec. 1996, pp. 406-410, vol. 19-No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83-No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.-No. 2, Supplement 1.

Swee Lian Tan, MD, PHD, FACS, Explanation of Infected Hemostatic Puncture Closure Devices—A Case Report, Vascular and Endovascular Surgery, 1999, pp. 507-510, vol. 33-No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9-No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42-No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5-No. 3-4.

UT Aker et al, Immediate arterial hemostasis after cardiac catheterization: initial experience with a new puncture closure device, Cathet Cardiovasc Diagn, Mar. 1994, pp. 228-232, vol. 33-No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19-No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25-No. 7 .

U.S. Appl. No. 10/435,104, filed Sep. 26, 2008, Notice of Allowance.
U.S. Appl. No. 10/541,083, filed Sep. 19, 2008, Notice of Allowance.
U.S. Appl. No. 10/616,832, filed Sep. 17, 2008, Office Action.
U.S. Appl. No. 11/198,811, filed Aug. 26, 2008, Office Action.
U.S. Appl. No. 11/406,203, filed Sep. 22, 2008, Notice of Allowance.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 10/006,400, filed Apr. 2, 2008, Office Action.
U.S. Appl. No. 10/147,774, filed Feb. 4, 2008, Notice of Allowance.
U.S. Appl. No. 10/147,774, filed Jun. 30, 2008, Office Action.
U.S. Appl. No. 10/264,306, filed May 26, 2005, Office Action.
U.S. Appl. No. 10/264,306, filed Feb. 4, 2008, Notice of Allowance.
U.S. Appl. No. 10/264,306, filed Jun. 27, 2008, Office Action.
U.S. Appl. No. 10/356,214, filed Mar. 6, 2008, Office Action.
U.S. Appl. No. 10/435,104, filed Apr. 4, 2008, Notice of Allowance.
U.S. Appl. No. 10/517,004, filed Jan. 30, 2008, Office Action.
U.S. Appl. No. 10/541,083, filed May 5, 2008, Office Action.
U.S. Appl. No. 10/638,115, filed Feb. 7, 2008, Office Action.
U.S. Appl. No. 10/667,144, filed May 12, 2008, Office Action.
U.S. Appl. No. 10/682,459, filed Apr. 2, 2008, Office Action.
U.S. Appl. No. 10/786,444, filed Apr. 24, 2008, Office Action.
U.S. Appl. No. 11/113,549, filed Apr. 16, 2008, Office Action.
U.S. Appl. No. 11/152,562, filed May 13, 2008, Office Action.
U.S. Appl. No. 11/344,891, filed Apr. 29, 2008, Office Action.
U.S. Appl. No. 11/406,203, filed May 23, 2008, Notice Of Allowance.
U.S. Appl. No. 11/411,925, filed Feb. 5, 2008, Office Action.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
U.S. Appl. No. 09/680,837, filed Jul. 9, 2002, Office Action.
U.S. Appl. No. 09/680,837, filed Nov. 6, 2002, Office Action.
U.S. Appl. No. 09/680,837, filed Mar. 25, 2003, Office Action.
U.S. Appl. No. 09/680,837, filed Jun. 16, 2003, Notice of Allowance.
U.S. Appl. No. 09/680,837, filed Sep. 11, 2003, Issue Notification.
U.S. Appl. No. 10/147,774, filed Mar. 18, 2009, Office Action.
U.S. Appl. No. 10/356,214, filed Apr. 29, 2009, Office Action.
U.S. Appl. No. 10/667,144, filed Mar. 24, 2009, Office Action.
U.S. Appl. No. 10/669,313, filed Oct. 31, 2005, Office Action.
U.S. Appl. No. 10/669,313, filed Jan. 11, 2006, Notice of Allowance.
U.S. Appl. No. 10/669,313, filed Jun. 28, 2006, Notice of Allowance.
U.S. Appl. No. 10/669,313, filed Nov. 15, 2006, Issue Notification.
U.S. Appl. No. 11/048,503, filed Mar. 13, 2009, Office Action.
U.S. Appl. No. 11/344,868, filed Mar. 25, 2009, Office Action.
U.S. Appl. No. 11/406,203, filed Mar. 3, 2009, Office Action.
U.S. Appl. No. 11/532,325, filed Feb. 23, 2009, Office Action.
U.S. Appl. No. 12/106,937, filed Mar. 30, 2009, Office Action.
U.S. Appl. No. 29/296,370, filed Apr. 1, 2009, Notice of Allowance.
U.S. Appl. No. 60/696,069, filed Jul. 1, 2005, Pantages et al.
U.S. Appl. No. 60/946,026, filed Jun. 25, 2007, Ellingwood.
McCarthy, et al., "Tension (Stay) Suture Bridge", J. of International College of Surgeons, 34(5), pp. 613-614 (Nov. 1960). cited by other.
U.S. Appl. No. 10/006,400, filed Jan. 2, 2009, Office Action.
U.S. Appl. No. 10/264,306, filed Feb. 26, 2009, Office Action.
U.S. Appl. No. 10/305,923, filed Nov. 1, 2004, Office Action.
U.S. Appl. No. 10/305,923, filed Mar. 3, 2005, Notice of Allowance.
U.S. Appl. No. 10/356,214, filed Nov. 4, 2008, Office Action.
U.S. Appl. No. 10/435,104, filed Nov. 14, 2007, Supplemental Notice of Allowance.
U.S. Appl. No. 10/435,104, filed Dec. 22, 2008, Supplemental Notice of Allowance.
U.S. Appl. No. 10/517,004, filed Aug. 13, 2008, Notice of Allowance.
U.S. Appl. No. 10/517,004, filed Feb. 10, 2009, Notice of Allowance.
U.S. Appl. No. 10/541,083, filed Oct. 31, 2007, Office Action.
U.S. Appl. No. 10/541,083, filed Dec. 29, 2008, Notice of Allowance.
U.S. Appl. No. 10/638,115, filed Oct. 29, 2008, Office Action.
U.S. Appl. No. 10/682,459, filed Dec. 4, 2008, Office Action.
U.S. Appl. No. 10/786,444, filed Oct. 17, 2008, Office Action.
U.S. Appl. No. 10/908,721, filed Nov. 25, 2008, Office Action.
U.S. Appl. No. 11/152,562, filed Feb. 13, 2009, Office Action.
U.S. Appl. No. 11/344,793, filed Jan. 22, 2009, Office Action.
U.S. Appl. No. 11/344,891, filed Dec. 8, 2008, Office Action.
U.S. Appl. No. 11/344,891, filed Feb. 26, 2009, Office Action.
U.S. Appl. No. 11/396,731, filed Feb. 13, 2009, Office Action.
U.S. Appl. No. 11/411,925, filed Jan. 12, 2009, Office Action.
U.S. Appl. No. 11/427,297, filed Jan. 30, 2009, Office Action.
U.S. Appl. No. 11/461,323, filed May 2, 2007, Office Action.
U.S. Appl. No. 11/461,323, filed Oct. 29, 2007, Office Action.
U.S. Appl. No. 11/461,323, filed Apr. 25, 2008, Office Action.
U.S. Appl. No. 11/461,323, filed Nov. 6, 2008, Office Action.
U.S. Appl. No. 11/744,089, filed Nov. 26, 2008, Office Action.
U.S. Appl. No. 12/106,928, filed Jan. 23, 2009, Office Action.
U.S. Appl. No. 29/296,370, filed Aug. 18, 2008, Office Action.
U.S. Appl. No. 29/296,370, filed Dec. 2, 2008, Notice of Allowance.
U.S. Appl. No. 10/006,400, filed Jul. 9, 2009, Notice of Allowance.
U.S. Appl. No. 10/517,004, filed Jun. 26, 2009, Notice of Allowance.
U.S. Appl. No. 10/541,083, filed Apr. 16, 2009, Notice of Allowance.

U.S. Appl. No. 10/638,115, filed May 7, 2009, Notice of Allowance.
U.S. Appl. No. 10/682,459, filed Jun. 10, 2009, Office Action.
U.S. Appl. No. 10/908,721, filed Jun. 23, 2009, Office Action.
U.S. Appl. No. 11/048,503, filed Jun. 26, 2009, Office Action.
U.S. Appl. No. 11/390,586, filed Jun. 24, 2009, Office Action.
U.S. Appl. No. 11/396,141, filed May 22, 2009, Office Action.
U.S. Appl. No. 11/396,731, filed May 22, 2009, Office Action.
U.S. Appl. No. 11/532,325, filed Jun. 17, 2009, Office Action.
U.S. Appl. No. 10/147,774, filed Oct. 26, 2009, Office Action.
U.S. Appl. No. 10/264,306, filed Aug. 13, 2009, Office Action.
U.S. Appl. No. 10/541,083, filed Sep. 30, 2009, Notice of Allowance.
U.S. Appl. No. 10/616,832, filed Jul. 21, 2009, Office Action.
U.S. Appl. No. 10/667,144, filed Nov. 23, 2009, Office Action.
U.S. Appl. No. 10/786,444, filed Jun. 18, 2009, Office Action.
U.S. Appl. No. 11/113,549, filed Jul. 21, 2009, Office Action.
U.S. Appl. No. 11/152,562, filed Jul. 6, 2009, Office Action.
U.S. Appl. No. 11/198,811, filed Sep. 2, 2009, Office Action.
U.S. Appl. No. 11/344,891, filed Oct. 7, 2009, Office Action.
U.S. Appl. No. 11/396,141, filed Aug. 26, 2009, Office Action.
U.S. Appl. No. 11/406,203, filed Sep. 16, 2009, Office Action.
U.S. Appl. No. 11/411,925, filed Sep. 10, 2009, Office Action.
U.S. Appl. No. 11/427,297, filed Sep. 15, 2009, Office Action.
U.S. Appl. No. 11/461,323, filed Jul. 27, 2009, Office Action.
U.S. Appl. No. 11/744,089, filed Aug. 14, 2009, Office Action.
U.S. Appl. No. 11/958,295, filed Aug. 27, 2009, Office Action.
U.S. Appl. No. 12/106,937, filed Nov. 18, 2009, Office Action.
U.S. Appl. No. 12/106,928, filed Oct. 5, 2009, Office Action.
U.S. Appl. No. 12/403,256, filed Dec. 16, 2009, Restriction Requirement.
U.S. Appl. No. 10/147,774, mailed Jun. 8, 2010, Office Action.
U.S. Appl. No. 10/264,306, mailed Jun. 15, 2010, Office Action.
U.S. Appl. No. 10/435,104, mailed Jun. 2. 2010, Office Action.
U.S. Appl. No. 10/667,144, mailed Jun. 22, 2010, Office Action.
U.S. Appl. No. 11/390,586, mailed Jul. 6, 2010, Office Action.
U.S. Appl. No. 11/396,731, mailed Jun. 29, 2010, Office Action.
U.S. Appl. No. 11/852,190, mailed Jun. 24, 2010, Office Action.
U.S. Appl. No. 12/113,851, mailed Jun. 24, 2010, Office Action.
U.S. Appl. No. 10/435,104, mailed Jul. 23, 2009, Notice of Allowance.
U.S. Appl. No. 10/669,313, mailed Oct. 31, 2005, Office Action.
U.S. Appl. No. 11/113,549, mailed Jul. 6, 2010, Office Action.
U.S. Appl. No. 11/959,334, mailed Jul. 23, 2010, Notice of Allowance.
U.S. Appl. No. 12/403,277, mailed Jul. 8, 2010, Office Action.
U.S. Appl. No. 11/344,891, mailed May 7, 2010, Office Action.
U.S. Appl. No. 12/106,928, mailed May 10, 2010, Office Action.
U.S. Appl. No. 12/113,851, mailed Apr. 27, 2010, Office Action.
U.S. Appl. No. 60/711,279, filed Aug. 24, 2005, Sibbitt, Jr. et al.
U.S. Appl. No. 60/726,985, filed Aug. 24, 2005, Sibbitt, Jr. et al.
U.S. Appl. No. 61/097,072, filed Sep. 15, 2008, Sibbitt, Jr. et al.
U.S. Appl. No. 11/316,775, mailed Apr. 16, 2008, Office Action.
U.S. Appl. No. 11/316,775, mailed Aug. 6, 2008, Office Action.
U.S. Appl. No. 11/406,203, mailed Jun. 18, 2010, Notice of Allowance.
U.S. Appl. No. 11/508,656, mailed Dec. 9, 2009, Office Action.
U.S. Appl. No. 11/508,656, mailed Mar. 25, 20010, Office Action.
U.S. Appl. No. 11/508,662, mailed Dec. 28, 2009, Office Action.
U.S. Appl. No. 11/508,662, mailed Apr. 14, 2010, Office Action.
U.S. Appl. No. 11/508,715, mailed Jan. 6, 2010, Office Action.
U.S. Appl. No. 11/508,715, mailed Apr. 26, 2010, Office Action.
U.S. Appl. No. 11/958,295, mailed May 25, 2010, Office Action.
U.S. Appl. No. 12/402,398, mailed May 20, 2010, Office Action.
U.S. Appl. No. 60/793,444, filed Apr. 20, 2006, Jones et al.
U.S. Appl. No. 60/693,531, filed Jun. 24, 2005, Carly.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.

Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Jan. 13, 2010, Notice of Allowance.
U.S. Appl. No. 10/006,400, mailed Apr. 27, 2010, Notice of Allowance.
U.S. Appl. No. 10/264,306, mailed Jan. 27, 2010, Office Action.
U.S. Appl. No. 10/356,214, mailed Jan. 13, 2010, Notice of Allowance.
U.S. Appl. No. 10/435,104, mailed Jan. 20, 2010, Notice of Allowance.
U.S. Appl. No. 10/517,004, mailed Jan. 11, 2010, Notice of Allowance.
U.S. Appl. No. 10/517,004, mailed Apr. 23, 2010, Notice of Allowance.
U.S. Appl. No. 10/541,083, mailed Feb. 5, 2010, Notice of Allowance.
U.S. Appl. No. 10/616,832, mailed Jan. 11, 2010, Notice of Allowance.
U.S. Appl. No. 10/638,115, mailed Dec. 1, 2009, Notice of Allowance.
U.S. Appl. No. 10/638,115, mailed Apr. 2, 2010, Notice of Allowance.
U.S. Appl. No. 10/682,459, mailed Dec. 23, 2009, Office Action.
U.S. Appl. No. 10/682,459, mailed Apr. 28, 2010, Office Action.
U.S. Appl. No. 10/786,444, mailed Jan. 14, 2010, Office Action.
U.S. Appl. No. 10/908,721, mailed Feb. 2, 2010, Office Action.
U.S. Appl. No. 11/048,503, mailed Jan. 11, 2010, Notice of Allowance.
U.S. Appl. No. 11/048,503, mailed Apr. 26, 2010, Notice of Allowance.
U.S. Appl. No. 11/152,562, mailed Mar. 31, 2010, Office Action.
U.S. Appl. No. 11/396,141, mailed May 4, 2010, Office Action.
U.S. Appl. No. 11/455,993, mailed Feb. 17, 2009, Office Action.
U.S. Appl. No. 11/455,993, mailed Dec. 16, 2009, Office Action.
U.S. Appl. No. 11/532,325, mailed Jan. 5, 2010, Office Action.
U.S. Appl. No. 11/532,576, mailed Mar. 1, 2010, Office Action.
U.S. Appl. No. 11/532,576, mailed Apr. 23, 2010, Office Action.
U.S. Appl. No. 11/674,930, mailed Jan. 8, 2009, Office Action.
U.S. Appl. No. 11/674,930, mailed Jun. 4, 2009, Office Action.
U.S. Appl. No. 11/674,930, mailed Jan. 8, 2010, Office Action.
U.S. Appl. No. 11/675,462, mailed Dec. 10, 2009, Office Action.
U.S. Appl. No. 11/767,818, mailed Dec. 24, 2009, Office Action.
U.S. Appl. No. 11/767,818, mailed Mar. 22, 2010, Office Action.
U.S. Appl. No. 11/959,334, mailed Aug. 19, 2009, Office Action.
U.S. Appl. No. 11/959,334, mailed Jan. 12, 2010, Notice of Allowance.
U.S. Appl. No. 11/959,334, mailed Apr. 14, 2010, Notice of Allowance.
U.S. Appl. No. 12/402,398, mailed Mar. 9, 2010, Office Action.
U.S. Appl. No. 12/403,256, mailed Mar. 30, 2010, Office Action.
U.S. Appl. No. 29/296,370, mailed Feb. 10, 2010, Issue Notification.
U.S. Appl. No. 10/356,214, mailed May 13, 2010, Notice of Allowance.
U.S. Appl. No. 10/616,832, mailed May 12, 2010, Notice of Allowance.
U.S. Appl. No. 10/541,083, mailed May 10, 2010, Notice of Allowance.
U.S. Appl. No. 11/198,811, mailed Jun. 29, 2010, Notice of Allowance.
U.S. Appl. No. 10/638,115, mailed Aug. 13, 2010, Notice of Allowance.
U.S. Appl. No. 12/403,256, mailed Aug. 19, 2010, Notice of Allowance.

* cited by examiner

CLOSURE DEVICE

This application is a continuation-in-part of U.S. application Ser. No. 10/335,075, filed Dec. 31, 2002, now U.S. Pat. No. 7,211,101 which is a continuation-in-part of U.S. patent application Ser. No. 10/081,726, filed Feb. 21, 2002 now U.S. Pat. No. 6,623,510 and is a continuation-in-part of U.S. patent application Ser. No. 10/435,104, filed May 9, 2003, and is a continuation-in-part of U.S. patent application Ser. No. 09/732,178, filed Dec. 7, 2000, U.S. Pat. No. 6,719,777 the disclosures of each of which are incorporated by reference herein.

FIELD OF THE INVENTION

The present invention relates generally to apparatus and methods for engaging tissue and/or closing openings through tissue, e.g., into body lumens, and more particularly to devices for closing a puncture in a blood vessel or other body lumen formed during a diagnostic or therapeutic procedure, and to methods for making and using such devices.

BACKGROUND

Catheterization and interventional procedures, such as angioplasty or stenting, generally are performed by inserting a hollow needle through a patient's skin and intervening tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

U.S. Pat. No. 5,478,354, issued to Tovey et al., discloses a surgical fastener including an annular base having legs that, in a relaxed state, extend in a direction substantially perpendicular to a plane defined by the base and slightly inwards toward one another. During use, the fastener is fit around the outside of a cannula, thereby deflecting the legs outward. The cannula is placed in an incision, and the fastener is slid along the cannula until the legs pierce into skin tissue. When the cannula is withdrawn, the legs move towards one another back to the relaxed state to close the incision.

U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. Sides of the ring may be squeezed to separate the barbs further, and the barbs may be engaged into tissue on either side of a wound. The sides may then be released, causing the barbs to return closer together, and thereby pulling the tissue closed over the wound. These staples, however, have a large cross-sectional profile and therefore may not be easy to deliver through a percutaneous site to close an opening in a vessel wall.

Accordingly, devices for engaging tissue, e.g., to close a vascular puncture site, would be considered useful.

SUMMARY OF THE INVENTION

Application Ser. No. 09/732,178, filed Dec. 7, 2000; Ser. No. 10/081,726, filed Feb. 21, 2002, now U.S. Pat. No. 6,623,510; Ser. No. 10/335,075, filed Dec. 31, 2002; Ser. No. 10/081,273, filed Feb. 21, 2002; Ser. No. 10/081,717, filed Feb. 21, 2002; Ser. No. 10/356,214, filed Jan. 30, 2003 and Ser. No. 10/638,118, filed Aug. 8, 2003, the disclosures of which are incorporated by reference herein, are directed to devices and methods for engaging tissue, e.g., to connect tissue segments together or to close and/or seal openings through tissue, such as in a wall of a body lumen. The present invention is directed to vascular closure devices or clips having a design particularly suitable for closing a puncture in a wall of a blood vessel formed during a diagnostic or therapeutic procedure.

According to the present invention, a device for engaging tissue includes a generally annular-shaped body defining a plane and disposed about a central axis extending substantially normal to the plane. The body may be movable from a substantially planar configuration lying generally in the plane towards a transverse configuration extending out of the plane. The body also includes a plurality of looped elements including alternating first and second curved regions that define an inner and outer periphery of the body, respectively, in the planar configuration. A plurality of tines or other tissue-engaging elements extend from the first curved regions, and are oriented towards the central axis in the planar configuration, and substantially parallel to the central axis in the transverse configuration. The device may be biased towards the planar configuration, e.g., to bias the tines towards the central axis.

The looped elements of the device may generally define an endless zigzag pattern, e.g., a sinusoidal pattern, extending about the central axis. The looped elements may facilitating deforming the device between the planar and transverse configurations, e.g., by distributing stresses through the device and minimizing localized stresses in the curved regions. In addition, the looped elements may be expandable between expanded and compressed states for increasing and reducing a periphery of the body in the transverse orientation, respectively. The looped elements may be biased towards one of the compressed and expanded states.

Adjacent tines of the device may have a first curved region disposed between them. The first curved region between adjacent tines may include a substantially blunt element extending towards the central axis. The blunt element may have a length shorter than lengths of the adjacent tines.

The tines of the device may include first and second primary tines, having a first length and a second length, respectively, which may be the same as or different than one another. The first and second primary tines may be disposed on opposing first curved regions, and may be oriented substantially towards each other in the planar configuration. In the planar configuration, the first and second primary tines may at least partially overlap the body or each other. The tines may also include one or more secondary tines having a length substantially shorter than the first and second lengths of the primary tines. The secondary tines may be disposed on either side of the first and second primary tines.

A first primary tine, having a first length, may extend from the body towards the central axis in the planar configuration, and may be deflectable out of the plane when the body is moved towards the transverse configuration. A second primary tine, having a second length, may extend from the body towards the first tine when the body is in the planar configuration, and may be deflectable out of the plane when the body is moved towards the transverse configuration. The lengths of the first and second primary tines may cause the primary tines to at least partially overlap in the planar configuration. The body may be biased towards the planar configuration to bias the tines generally towards the central axis.

The device may include a set of secondary tines having a length shorter than the first and second lengths. The secondary tines may extend from the body towards the central axis in the planar configuration, and may be deflectable out of the plane when the body is moved towards the transverse configuration. In an exemplary embodiment, a secondary tine may be disposed on either side of the first primary tine, and a secondary tine may be disposed on either side of the second primary tine.

Optionally, adjacent tines may have a first curved region disposed between them. The first curved region between adjacent tines may include a substantially blunt element extending towards the central axis. The blunt element may have a length shorter than lengths of the adjacent tines.

Also, the device may include a plurality of looped elements disposed around a periphery of the body. The looped elements may generally define an endless zigzag pattern extending about the central axis. The first primary tine and the second primary tine may extend from looped elements disposed opposite one another. The looped elements may be expandable between expanded and compressed states for increasing and reducing a periphery of the body in the transverse orientation, respectively. The looped elements may be biased towards one of the compressed and expanded states.

In any event, the primary tines of the clips of the present invention will be offset from the axis of symmetry of the loop from which they extend. The offsetting of the primary tines is achieved by simply relocating the primary tines which are directly attached to the loop to a location which is not on the axis of symmetry of the loop or providing an intermediate connecting element between the tines and the axis of symmetry of the curved region of the loop from which the tine extends. This connecting element is preferably straight or linear, but may also be curved. It is particularly preferred to use such a connecting element which is connected to a point or region on the axis of symmetry of the loop to enhance consistency of performance of the clip during deployment. The offsetting of the tines is believed to reduce any tendency to wander during deployment, which the tines might otherwise have.

In another aspect of the present invention, a method is provided for manufacturing a clip from an elastic material, such as a sheet of superelastic alloy, e.g., a nickel-titanium alloy ("Nitinol"). The components of the clip, e.g., a generally-annular body, optionally including looped elements, and/or tines, may be formed by removing portions from the sheet. The portions may be removed, e.g., by laser cutting, chemical etching, photo chemical etching, stamping, electrical discharge machining, and the like, or by the method disclosed in U.S. patent application Ser. No. 10/335,075, filed Dec. 31, 2002. The clip may be polished using one or more processes, such as electro-polishing, chemical etching, tumbling, sandblasting, sanding, and the like, and/or heat-treated to provide a desired finish and/or desired mechanical properties. Optionally, the body and tines may be coated with a therapeutic agent, e.g., a peptide coating and/or one or more clotting factors.

In addition or alternatively, the clip may be disposed in a planar configuration, e.g., upon forming the clip from the sheet, and heat treated to form a clip biased to the planar configuration. For example, the clip may be formed from a shape memory material, e.g., Nitinol, that may substantially recover the planar configuration when heated to a first predetermined temperature corresponding to an austenitic state, e.g., a temperature close to body temperature. The clip may be cooled to a second predetermined temperature corresponding to a martensitic state, e.g., a temperature at or below ambient temperature, and malleably manipulated.

For example, the clip formed from the sheet may be deformed to a transverse configuration, such as that described above, e.g., by loading the clip onto a mandrel or directly onto a delivery device. If the clip includes looped elements formed from the body, the looped elements may be biased upon heat treatment towards an expanded state, but may be malleably deformed to a compressed state upon cooling, e.g., to facilitate loading onto the delivery device. Alternatively, the clip may be formed from a superelastic material, e.g., Nitinol, such that the clip may be resiliently deformed to the transverse configuration and/or compressed state, yet may automatically attempt to resume its planar configuration and/or expanded state upon release from external forces.

The clip may also be manufactured according to the method set forth in U.S. patent application Ser. No. 10/335, 075, filed Dec. 31, 2002.

In still another aspect of the present invention, a method for closing an opening in a wall of a body lumen is provided. The distal end of an elongate member may be advanced through an opening in a patient's skin, along a passage through tissue, and into the body lumen. A distal portion of an obturator may be positioned distally beyond the distal end of the elongate member along the passage within the body lumen. One or more expandable elements on the distal portion of the obturator may be expanded transversely. The obturator may be withdrawn from the passage until the expandable elements contact the wall of the body lumen, thereby providing a tactile indication of a location of the wall of the body lumen between the elongate member and the plurality of expandable elements of the obturator.

A clip may be advanced into the passage over the elongate member until tines of the clip penetrate the wall of the body lumen, the tines and the expandable elements on the obturator being angularly offset from one another such that the tines penetrate the wall at locations between the expandable elements. The obturator may be collapsed, and the elongate member and/or obturator may be withdrawn from the body lumen and passage, leaving the clip to substantially close the opening in the wall of the body lumen. When the elongate member is withdrawn, the tines may automatically at least partially move towards a planar configuration to substantially close the opening. The clip may also be delivered to the desired site by using the apparatus and methods disclosed in U.S. patent application Ser. No. 10/356,214, filed Jan. 30, 2003 and Ser. No. 10/638,118, filed Aug. 8, 2003.

Advancing the clip may include puncturing the wall of the body lumen with the primary tines until tips of the primary tines enter the body lumen, and puncturing the wall of the body lumen with the secondary tines. The primary tines and the secondary tines may puncture the walls without contacting the expandable elements of the obturator.

Other objects and features of the present invention will become apparent from consideration of the following description taken in conjunction with the accompanying drawings.

DETAILED DESCRIPTION OF THE PREFERRED EMBODIMENTS

Figure 1A:
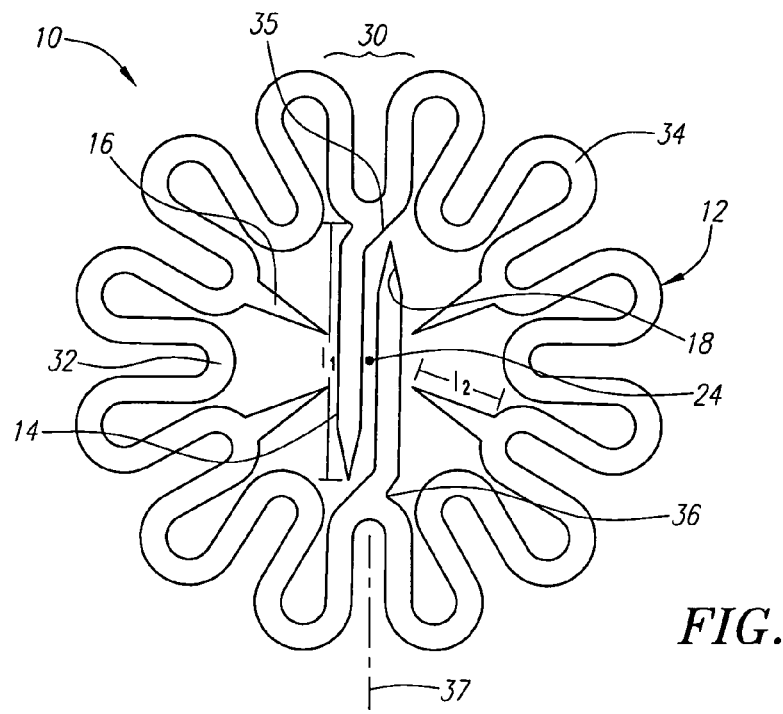
FIG. 1A is a top view of a clip including a plurality of tines in a planar orientation, in which the primary tines are offset from the axis of symmetry of the loop from which they extend and are connected to a curved region of the loop by a straight connecting element in accordance with the present invention.
Figure 1B:
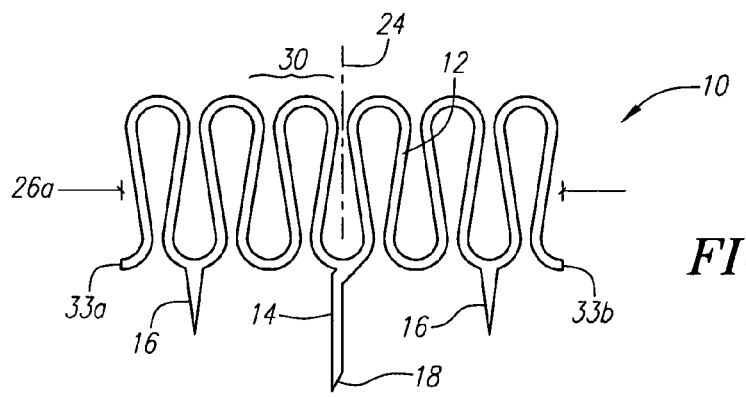
FIGS. 1B and 1C are side views of the clip of FIG. 1A, with the tines oriented substantially transversely from the planar orientation, in compressed and expanded states, respectively.
Figure 1C:
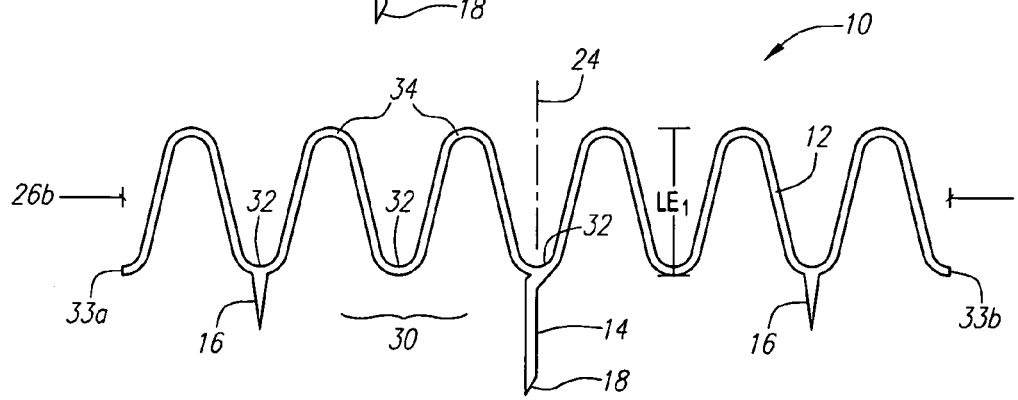

Turning now to the drawings, FIGS. 1A-1C show a first preferred embodiment of a closure device or clip 10 for closing an incision, puncture, or other passage through tissue, e.g., communicating with a blood vessel or other body lumen (not shown). The clip 10 includes a body 12, which may be generally annular in shape and surrounds a central axis 24, a plurality of primary tines 14 and a plurality of secondary tines 16 extending from the body 12. As used herein, an "annular-shaped body" includes any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis.

The body 12 includes a plurality of looped or curved elements 30 that are connected to one another to form the body 12. Each looped element 30 may include an inner or first curved region 32 and an outer or second curved region 34. In a preferred embodiment, the first and second curved regions 32, 34 are out of phase with one another and are connected alternately to one another, thereby defining an endless sinusoidal pattern. Alternatively, other generally zigzag patterns may be provided that repeat periodically, e.g., saw tooth or square tooth patterns (not shown), instead of a sinusoidal pattern, thereby defining inner and outer regions that alternate about the body 12.

The plurality of tines 14 and 16 may be biased to extend generally inwardly, e.g., towards one another and/or towards the central axis 24. The tines 14 and 16 may be disposed on the first curved regions 32, and oriented toward the central axis 24 when the clip 10 is in the planar configuration. The primary tines 14 are offset from the axis of symmetry 37 of the loops from which they extend and are connected to a fist curved region 32 by a straight connecting element having a longer side 35 and a shorter side 36. In a preferred embodiment, the tines 14 and 16 may be provided in pairs opposite from one another or provided otherwise symmetrically with respect to the central axis 24.

The tines 14 and 16 may include a variety of pointed tips, such as a bayonet tip, and/or may include barbs (not shown) for penetrating or otherwise engaging tissue. For example, to increase the penetration ability of the clip 10 and/or to lower the insertion force required to penetrate tissue, each primary tine 14, as shown in FIG. 1A as element 18, and each secondary tine 16 may include a tapered edge (not shown) extending towards the tip along one side of the tine 14 or 16. Alternatively, as shown in FIGS. 1A-1C, each tine 14 or 16 may be provided with a tapered edge on each side of the tine 14 or 16 extending towards the tip.

Additionally, as shown in FIGS. 1A-1C, the tines 14 and 16 may be disposed on alternating first curved regions 32. Thus, at least one period of a zigzag pattern may be disposed between adjacent tines 14 and 16, which may enhance flexibility of the clip 10, as explained further below.

As shown in FIGS. 1B and 1C (where opposite ends 33a, 33b are connected to one another), the body 12 and/or the tines 14 and 16 may be deflected such that the tines 16 extend transversely with respect to the plane defined in the planar configuration, thereby defining a transverse configuration for the clip 10. Preferably, the tines 14 and 16 are oriented substantially parallel to the central axis 24 in the transverse configuration, as shown in FIG. 1B. In the transverse configuration, the body 12 may have a generally annular shape defining a length, $LE_1$, that extends generally parallel to the central axis 24, and corresponds generally to an amplitude of the zigzag pattern. Preferably, the body 12 is sufficiently flexible such that the clip 10 may assume a generally circular or elliptical shape (not shown), e.g., conforming to an exterior surface of a delivery device (not shown) used to deliver the clip 10.

In a preferred embodiment, the tines 14 and 16 and/or body 12 are biased to move from the transverse configuration towards the planar configuration of FIG. 1A. Thus, with the tines 14 and 16 in the transverse configuration, the tines 14 and 16 may penetrate and/or be engaged with tissue at a puncture site. When the clip 10 is released, the tines 14 and 16 may attempt to return towards one another as the clip 10 moves towards the planar configuration, thereby drawing the engaged tissue together and substantially closing and/or sealing the puncture site, as explained further below.

The looped elements 30 may distribute stresses in the clip 10 as it is deformed between the planar and transverse configurations, thereby minimizing localized stresses that may otherwise plastically deform, break, or otherwise damage the clip 10 during delivery. In addition, when the clip 10 is in the transverse configuration, the looped elements 30 may be movable between a compressed state, such as that shown in FIG. 1B, and an expanded state, such as that shown in FIG. 1C. Preferably, the looped elements 30 are biased towards the expanded state, but may be compressed to the compressed state, e.g., by constraining the clip 10. Alternatively, only a portion of the looped elements 30 may be biased towards the expanded state, e.g., the first curved regions 32, and/or the looped elements 30 may be biased towards the compressed state. Furthermore, the looped elements 30 reduce the force required to be exerted on the clip 10 to transition the clip 10 from the planar configuration to the transverse configuration before loading onto a delivery device (not shown).

With the clip 10 in the transverse configuration, the looped elements 30 may be circumferentially and/or radially compressed to the compressed state until the clip 10 defines a first diameter or circumference 26a, such as that shown in FIG. 1B. The clip 10 may be constrained in the compressed state, e.g., by loading the clip 10 onto a carrier assembly of a delivery device (not shown), as described further below. When released from the constraint, e.g., when deployed from the carrier assembly, the clip 10 may automatically expand towards the expanded state, such as that shown in FIG. 1C, thereby defining a second diameter or circumference 26b. Thus, the looped elements 30 may facilitate reducing the profile of the clip 10 during delivery, e.g., to facilitate introducing the clip 10 through a smaller puncture or passage. Once the clip 10 is deployed entirely from the delivery device, the looped elements 30 may resiliently expand as the clip 10 returns towards the planar configuration, as explained further below.

To manufacture the clip 10 (or, similarly, any of the other clips described herein), the body 12 and the tines 14 and 16 may be integrally formed from a single sheet of material, e.g., a superelastic alloy, such as a nickel-titanium alloy ("Nitinol"). Portions of the sheet may be removed using conventional methods, such as laser cutting, chemical etching, photo chemical etching, stamping, using an electrical discharge machine (EDM), and the like, or the method disclosed in U.S. patent application Ser. No. 10/335,075, filed Dec. 31, 2002, to form the clip. The tines 14 and 16 may be sharpened to a point, i.e., tips may be formed on the tines 14 and 16 using conventional methods, such as chemical etching, mechanical grinding, and the like.

The clip 10 may be polished to a desired finish using conventional methods, such as electro-polishing, chemical etching, tumbling, sandblasting, sanding, and the like. Polishing may perform various functions depending on the method used to form the clip 10. For a clip formed by laser cutting or using an EDM, polishing may remove heat affected zones (HAZ) and/or burrs from the clip. For a clip formed by photo chemical etching, polishing may create a smoother surface finish. For a clip formed by stamping, polishing may remove or reduce burrs from the bottom side of the clip, and/or may smooth the "roll" that may result on the topside of the clip from the stamping process.

In addition or alternatively, the clip 10 may be formed from a shape memory alloy, e.g., Nitinol, with the looped elements 30 formed initially in the compressed state and/or the clip 10 in the planar configuration. With the clip 10 deformed to the transverse configuration, the clip 10 may be expanded, e.g., by applying a force radially outwards against an inner surface of the clip 10, thereby expanding the looped elements 30 to the expanded state. The looped elements 30 may then be heat treated, e.g., by heating the clip 10 to an austenitic state, to cause the looped elements 30 to "remember" the expanded state, as is known to those skilled in the art. It may also be necessary to further heat treat the clip 10 further, e.g., with the tines in the planar configuration to cause the body 12 and/or tines 14 and 16 to "remember" and be biased towards the planar configuration, as is known to those skilled in the art. The clip 10 may then be cooled, e.g., to a martensitic state, which may be at or close to ambient temperature, and manipulated, e.g., malleably deformed to the transverse configuration, for example, by loading the clip 10 onto a delivery device (not shown), as described below. Thus, if the clip 10 is subsequently heated to a predetermined temperature, e.g., at or below body temperature, the material may remember the planar configuration and/or expanded state and become biased towards them.

Each of the primary tines 14 may have a length $l_1$, although alternatively, as shown in FIG. 1A, each of the primary tines 14 may have a different length than one another. The primary tines 14 may be disposed in one or more opposing pairs, e.g., on opposing first curved regions 32, and may be oriented towards and/or across the central axis 24 in the planar configuration. In the planar configuration, the lengths $l_1$ may be sufficiently long such that the primary tines 14 at least partially overlap one another, i.e., extend across the central axis 24 towards an opposing tine 14. Therefore, the tips of the primary tines 14 may extend past the central axis 24 and/or the primary tines 14 in each pair may lie substantially parallel to each other when the clip 10 is in the planar configuration.

Each of the secondary tines 16 may be disposed on a first or inner curved region 32, e.g., such that one or more secondary tines 16 may be provided between opposing pairs of primary tines 14. Each of the secondary tines 16 may have a length 12 that is substantially less than the length $l_1$ of the primary tines 14.

Preferably, a secondary tine 16 is disposed on either side of each primary tine 14. For example, the clip 10 shown in FIGS. 1A-1C has first and second primary tines 14, and each of the first and second primary tines 14 has a secondary tine 16 on either side of it. Thus, the clip 10 may have a total of two primary tines 14 and four secondary tines 16. Optionally, the secondary tines 16 may be disposed substantially symmetrically about the central axis 24. The tines 14, 16 may be provided on every other first curved regions 32. For example, a first curved region 32 having neither a primary tine 14 nor a secondary tine 16 may separate each adjacent tine, e.g., between two adjacent secondary tines 16, or between a secondary tine 16 and a primary tine 14.

With the clip 10 in the transverse configuration, the clip 10 may be delivered such that the primary tines 14 entirely penetrate the wall of a blood vessel or other body lumen, while the secondary tines 16 only partially penetrate the wall due to their relative lengths, as explained further below.

As shown in FIG. 1A, primary tines 14 are connected to curved regions 32 by linear regions 35 and 36 which are of different lengths. Thus, primary tines 14 are offset from the axis of symmetry 37 of the loops having the curved regions to which they are attached. The offsetting of primary tines is also disclosed in parent application Ser. No. 10/335,075, filed Dec. 31, 2002, which discloses the use of curved configurations to connect the primary tines to the curved regions of the clip. It has been found preferable to use linear, or straight, regions, as shown as elements 35 and 36 in FIG. 1A to connect the primary tines 14 of the present invention to the curved regions 32.

Figure 2:
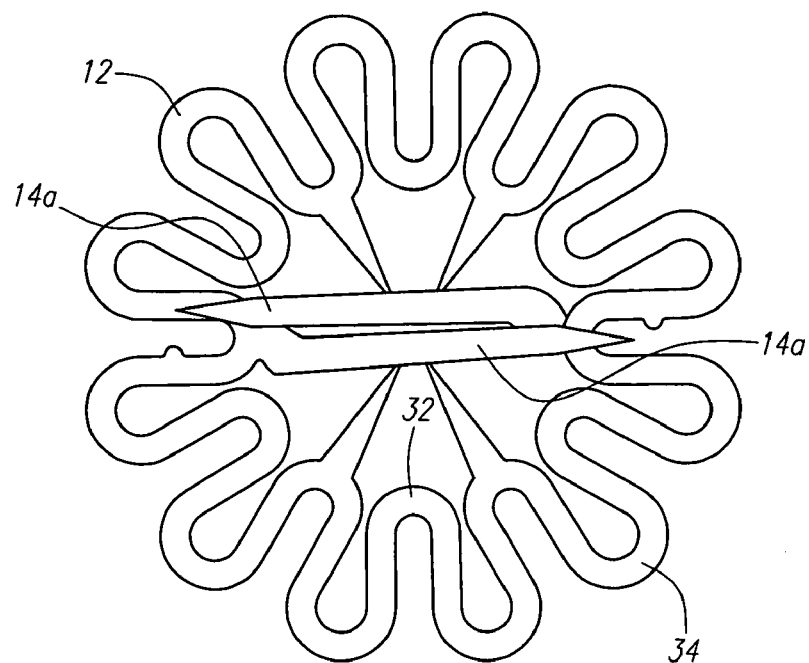
FIG. 2 illustrates a clip according to the present invention in which the primary tines overlap with the body of the clip.

FIG. 2 illustrates a clip of the same general type as that of FIG. 1A, but in a somewhat different embodiment in which primary tines 14a overlap body 12 at locations comprising first curved regions 32.

Figure 3A:
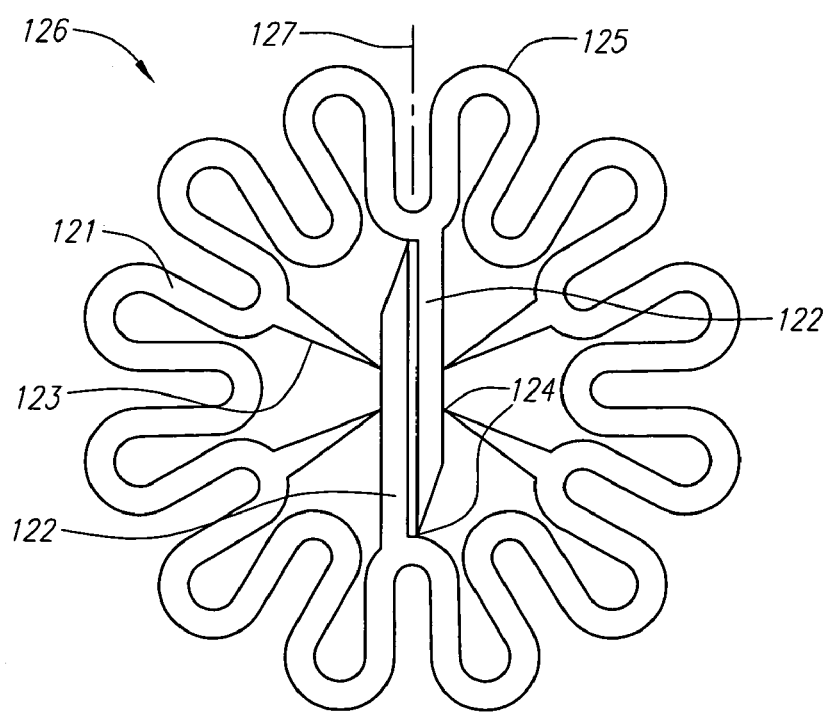
FIGS. 3A-3C illustrate top views of clips in which the primary tines are offset from the axis of symmetry of the loop from which they extend by a connecting element which is at least partially curved.
Figure 3B:
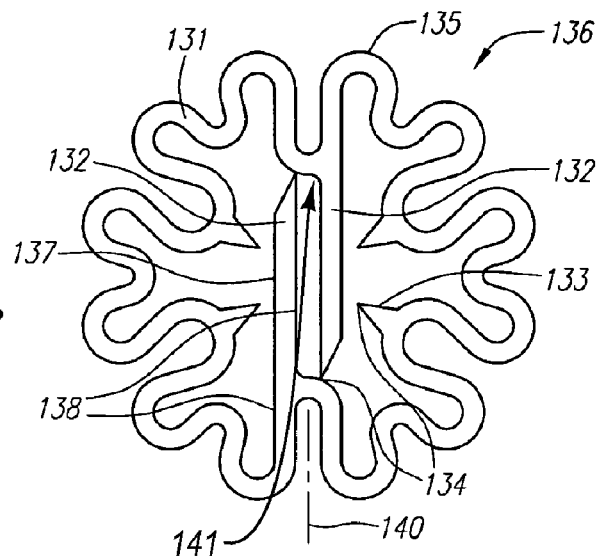
Figure 3C:
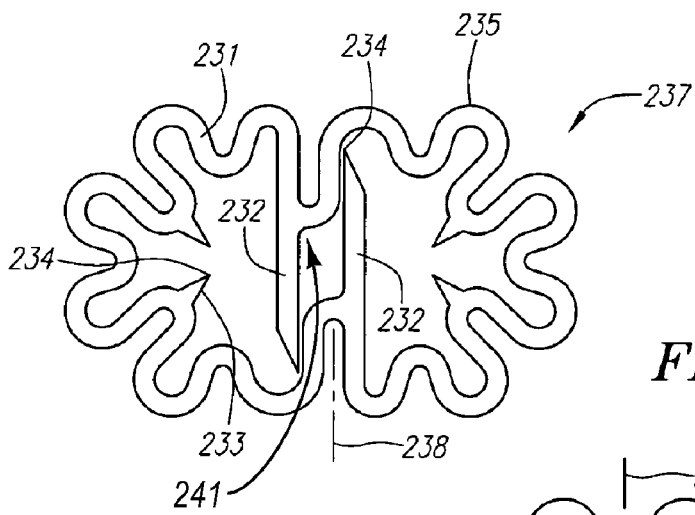

FIGS. 3A-3C illustrate various designs of clips configured according to the present invention in which the primary tines, which are offset from the axis of symmetry of the loop from which they extend, are connected directly to a first curved region or are connected to the curved region by extending one side of the curved region to form one side of the primary tine and connecting the other side of the primary tine with a curved connecting element 141 and 241, as shown in FIGS. 3B and 3C.

Turning to FIGS. 3A-3C in more detail, FIG. 3A illustrates clip 126 has body 121, primary tines 122, secondary tines 123 and loops 125. Each loop has an axis of symmetry such as that indicated by 127. The tines are provided with point 124. In this embodiment, the primary tines 122 are offset from the axis of symmetry of the loop from which they extend and are connected directly to the first curved section of such loop.

In FIG. 3B, the clip 136 has body 131 having primary tines 132 and secondary tines 133 is illustrated. The body 131 is provided with loops 135 and the primary tines 132 comprise a first side 137 which is an extension of a side of the loop 138 from which tine 137 extends and another side 139 which is connected directly to the loop from which it extends. The primary tines are offset from the axis of symmetry, indicated by 140 of the loop from which they extend.

The clip of FIG. 3C is similar in some respects to the clip of 3B, but is generally elliptical in shape rather than generally circular in shape. Thus, clip 237 comprises body 231 which has loops 235, primary tines 232, secondary tines 233 which tines have points 234. In this embodiment, the primary tines 232 extend beyond the innermost reach of the first curved regions which are opposite the first curved regions from which the primary tines extend. The primary tines are offset from the axis of symmetry 238 of the loop from which they extend. The primary tines of the clip of FIG. 3C are connected to the loops from which they extend in the same manner as those of FIG. 3B.

Figure 4:
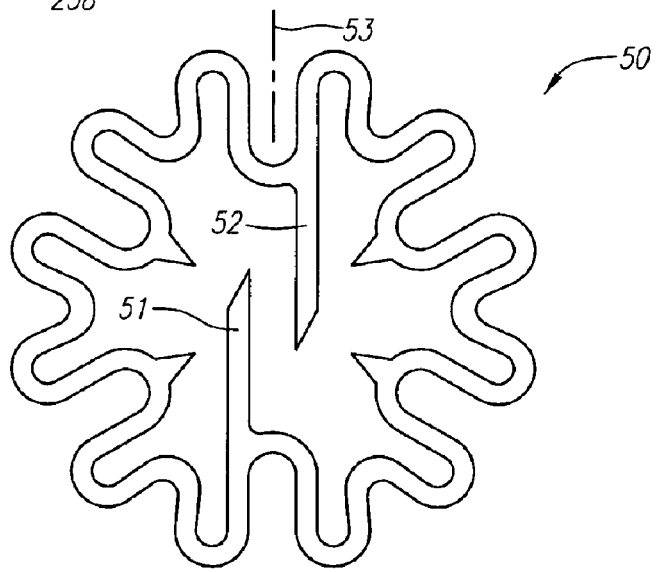
FIG. 4 illustrates a clip in which the primary tines have different lengths.

FIG. 4 illustrates a clip 50 in which the primary tines 51 and 52 are of different lengths. The primary tines 51 and 52 are offset from the axis of symmetry 53 of the loop from which they extend and are connected to the loop in the same manner as the primary tines of FIG. 3B.

Any of the clips of the present invention may include one or more radiopaque markers or other markers visible using external imaging, such as fluoroscopy. For example, using the clip 10 of FIGS. 1A-1C as an example, the entire clip 10 may be coated with radiopaque material, which may be a high density material such as gold, platinum, platinum/iridium, and the like.

Alternatively, the clip 10 may be partially coated with radiopaque material by using masking techniques. For example, the entire clip 10 may first be coated with radiopaque material. The clip 10 may then be masked at locations where the radiopaque coating is desired. For example, the looped elements 30 of the clip 10 may be left unmasked during this process if it is desired to leave the looped elements 30 uncoated by radiopaque material. This may be desirable, e.g., to prevent radiopaque material from adversely affecting the flexibility of the looped elements 30. The clip 10 may then be treated to remove the radiopaque material from the unmasked areas, in this example, the looped elements 30. The masking may then be removed using conventional processes, leaving the rest of the clip 10 coated with radiopaque material.

In another alternative, one or more discrete markers may be provided at predetermined locations on the clip 10. For example, high density or radiopaque material may be crimped or otherwise secured onto opposing double looped or circular regions 30. In another embodiment, a plurality of pockets may be provided on the looped elements 30 into which high density plugs (not shown) may be bonded or otherwise secured. These various radiopaque markers may also be incorporated in any of the embodiments described herein.

Any of the clips of the present invention may be coated with a substance that enhances hemostasis and/or healing of a blood vessel, e.g., by increasing a rate of regeneration of endothelium on the interior surface of the vessel, or by decreasing inflammatory response at the treatment site. In one embodiment, a suitable synthetic peptide coating may be applied to a clip to attract endothelial cells to the surface. An exemplary synthetic peptide coating may, for example, attach to the same cell binding sites as collagen. In another embodiment, a clip may be coated with a combination of clotting factors in order to promote hemostasis. For example, one side of the clip may be coated with Factor III and an endopeptidase, such as PTA, to accelerate the intrinsic clotting pathway. On the opposite side of the clip, a combination of a protein cofactor proaccelerin (Factor V) and an activated endopeptidase, such as serum prothrombin conversion accelerator (SPCA), cothromboplastin, and the like, may be applied to accelerate the extrinsic clotting pathway. The clips of the present invention may also be coated with any suitable hydrophilic polymer that swells in the presence of bodily fluids in order to reduce, minimize, or stop blood flow, thereby aiding the hemostasis process.

The clips of the present invention may be delivered using various apparatus and methods. Suitable apparatus that may be used to deliver a clip of the present invention are disclosed in co-pending U.S. application Ser. No. 10/081,723, filed on Feb. 21, 2002 and entitled "Apparatus and Methods for Delivering a Closure Device" and in U.S. application Ser. No. 10/356,214, filed Jan. 30, 2003 and Ser. No. 10/638,118, filed Aug. 8, 2003, and Ser. No. 10/081,725, filed Feb. 2, 2001, which are assigned to the assignee of the present application. The disclosures of these applications and any references cited therein are expressly incorporated by reference herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for engaging tissue, comprising:
   a generally annular-shaped body defining a plane and disposed about a central axis extending substantially normal to the plane, the body being movable from a substantially planar configuration lying generally in the plane towards a transverse configuration extending out of the plane, the body being biased to return toward the planar configuration from the transverse configuration, the body comprising a plurality of looped elements comprising alternating first and second curved regions;
   at least one first primary tine extending from a first curved region of a looped element of the annular-shaped body generally towards the central axis in the planar configuration and being deflectable out of the plane when the body is moved towards the transverse configuration;
   at least one second primary tine extending from another first curved region of a looped element of the annular-shaped body towards the first primary tine when the body is disposed in the planar configuration; and
   said first and second primary tines being offset from and substantially parallel to an axis of symmetry of the looped element from which they extend, said first and second primary tines being substantially parallel to each other.

2. The device of claim 1, wherein the body is biased towards the planar configuration for biasing the primary tines generally towards the central axis.

3. The device of claim 1, further comprising:
a set of secondary tines having lengths shorter than a first length of the at least one first primary tine and a second length of the at least one second primary tine, the secondary tines extending from the annular-shaped body generally towards the central axis in the planar configuration and being deflectable out of the plane when the body is moved towards the transverse configuration.

4. The device of claim 1, wherein the at least one first primary tine, the at least one second primary tine, and the body are formed from a single sheet of material.

5. The device of claim 4, wherein the sheet of material comprises a superelastic alloy.

6. The device of claim 1, wherein the looped elements generally define an endless zigzag pattern extending about the central axis.

7. The device of claim 6 wherein the endless zigzag pattern comprises a generally sinusoidal pattern.

8. The device of claim 1, wherein the at least one first primary tine and the at least one second primary tine extend from first curved regions disposed opposite one another.

9. The device of claim 8, further comprising a set of secondary tines having lengths shorter than a first length of the at least one first primary tine and a second length of the at least one second primary tine, the secondary tines extending from the annular-shaped body generally towards the central axis in the planar configuration and being deflectable out of the plane when the body is moved towards the transverse configuration, each pair of adjacent tines having a first curved region disposed therebetween.

10. The device of claim 9, wherein a secondary tine is disposed on either side of the at least one first primary tine, and a secondary tine is disposed on either side of the at least one second primary tine.

11. The device of claim 1, wherein the plurality of looped elements are expandable between expanded and compressed states for increasing and reducing, respectively, a periphery of the body in the transverse orientation.

12. The device of claim 11, wherein the plurality of looped elements are biased towards the compressed state.

13. The device of claim 1 wherein said first and second primary tines are connected to said first curved regions of said looped elements by a connector element.

14. The device of claim 13 wherein said connector element is curved.

15. The device of claim 13 wherein said connector element is straight.

16. The device of claim 15 wherein the at least one first primary tine overlaps the first curved region which is opposite the first curved region from which the at least one first primary tine extends and the at least one second primary tine overlaps the first curved region which is opposite the first curved region from which the at least one second primary tine extends.

17. The device of claim 1 wherein said first curved regions define an inner periphery of the body and the second curved regions define an outer periphery of the body when the body is in the planar configuration.

18. The device of claim 1 wherein at least one of said at least one first primary tine and said at least one second primary tine is connected to the first curved region by a curved connecting element.

19. The device of claim 1 wherein the at least one first primary tine overlaps the first curved region which is opposite the first curved region from which the at least one first primary tine extends and the at least one second primary tine overlaps the first curved region which is opposite the first curved region from which the at least one second primary tine extends.

20. A device for engaging tissue, comprising:
a generally annular-shaped body defining a plane and disposed about a central axis extending substantially normal to the plane, the body being movable from a substantially planar configuration lying generally in a plane towards a transverse configuration extending at an angle through the plane, the body being biased to return to the planar configuration from the transverse configuration, the body comprising a plurality of looped elements comprising alternating first and second curved regions, the first curved regions defining an inner periphery of the body and the second curved region defining an outer periphery of the body when it is in the planar configuration;
at least one first primary tine extending from a first curved region generally toward the central axis in the planar configuration and being deflectable out of the plane when the body is moved towards the transverse configuration;
at least one second primary tine extending from another first curved region towards the central axis and being deflectable out of the plane when the body is moved towards the transverse configuration; and
said first and second primary tines being offset from and substantially parallel to an axis of symmetry of the looped element from which they extend, said first and second primary tines being substantially parallel to each other.

21. The device of claim 20 wherein at least one of said at least one first primary tine and said at least one second primary tine is connected to the first curved region by a straight connecting element.

22. The device of claim 21 wherein the at least one first primary tine overlaps the first curved region which is opposite the first curved region from which the at least one first primary tine extends and the at least one second primary tine overlaps the first curved region which is opposite the first curved region from which the at least one second primary tine extends.

23. The device of claim 20 wherein the at least one first primary tine overlaps the first curved region which is opposite the first curved region from which the at least one first primary tine extends and the at least one second primary tine overlaps the first curved region which is opposite the first curved region from which the at least one second primary tine extends.

* * * * *